United States Patent [19]
Haber et al.

[11] Patent Number: 5,919,930
[45] Date of Patent: Jul. 6, 1999

[54] PROCESS FOR CROSS-COUPLING AROMATIC BORON COMPOUNDS WITH AROMATIC HALOGEN COMPOUNDS OR PERFLUOROALKYLSULFONATES

[75] Inventors: Steffen Haber, Germersheim; Javier Manero, Frankfurt, both of Germany

[73] Assignee: Hoechst Aktiengesellschaft, Frankfurt, Germany

[21] Appl. No.: 08/506,892

[22] Filed: Jul. 26, 1995

[30] Foreign Application Priority Data

Jul. 28, 1994 [DE] Germany .............................. 44 26 671

[51] Int. Cl.$^6$ ....................... C07D 213/26; C07D 239/30
[52] U.S. Cl. ..................... 544/238; 544/224; 544/242; 544/315; 544/316; 544/333; 544/334; 544/335; 544/360; 544/364; 544/395; 544/405; 544/409; 544/403; 544/410; 546/302; 546/303; 546/261; 546/239; 546/259; 546/268.7; 546/286; 546/192; 546/269.7; 546/339; 546/345; 546/193
[58] Field of Search ...................... 544/238, 333, 544/334, 335, 310, 409; 546/339, 345, 302, 239, 259; 548/237

[56] References Cited

U.S. PATENT DOCUMENTS

| | | | |
|---|---|---|---|
| 4,087,452 | 5/1978 | Kuntz ....................................... | 260/464 |
| 4,219,677 | 8/1980 | Kuntz ....................................... | 568/657 |
| 4,483,802 | 11/1984 | Gartner et al. ....................... | 260/505 C |
| 5,043,510 | 8/1991 | Casalnuovo et al. .................... | 585/466 |

FOREIGN PATENT DOCUMENTS

| | | |
|---|---|---|
| 0 354 434 | 2/1990 | European Pat. Off. . |
| 0 470 795 | 2/1992 | European Pat. Off. . |
| 42 36 103 | 4/1994 | Germany . |
| 43 40 490 | 6/1994 | Germany . |
| WO 94/00423 | 1/1994 | WIPO . |

OTHER PUBLICATIONS

Casalnuovo, Albert L., et al., "Palladium–Catalyzed Alkylations in Aqueous Media", *J. Am. Chem. Soc.* 1990, 112, 4324–4330.

Genet, Jean Pierre, et al., "Palladium–Catalyzed Cross–Coupling Reactions in a Homogeneous Aqueous Medium", *SYNLETT* 1992, 715–717.

Miyaura, N., et al., "The Palladium–Catalyzed Cross–Coupling Reaction of Phenylboronic Acid with Haloarenes in the Presence of Bases", *Synthetic Communications* 1981, 11(7), 513–519.

Wakefield, Organolithium Methods, pp. 149–158, 1989.
German Abstract No. 4236103–A published Oct. 26, 1992.
German Abstract No. 4340490–A published Sep. 3, 1993.
German Abstract No. 9400423–A published May 15, 1993.
Synlett, Sep. 1992, pp. 715–717 entitled "Palladium–Catalyzed Cross Coupling Reactions in a Homogenous Aqueous Medium", by Genet et al.

J. Am. Chem. Soc. 1990, 112, pp. 4324–4330 entitled "Palladium–Catalyzed Alkylations in Aqueous Media", by Casalnuovo et al.

*Primary Examiner*—Mukund J. Shah
*Assistant Examiner*—Deepak R. Rao
*Attorney, Agent, or Firm*—Frommer Lawrence & Haug LLP

[57] ABSTRACT

Process for cross-coupling aromatic boron compounds with aromatic halogen compounds or perfluoroalkylsulfonates.

In a process for preparing polycyclic aromatic compounds by cross-coupling aromatic boron compounds with aromatic halogen compounds or perfluoroalkylsulfonates under palladium catalysis in the presence of at least one water-soluble complex ligand, the reaction medium comprises an aqueous and an organic phase and the palladium is added in the form of a palladium compound soluble in the organic phase.

Polycyclic aromatic compounds can thus be prepared economically and in very good yields and simultaneously very high purity, in particular without contamination by the complexing ligands.

12 Claims, No Drawings

PROCESS FOR CROSS-COUPLING AROMATIC BORON COMPOUNDS WITH AROMATIC HALOGEN COMPOUNDS OR PERFLUOROALKYLSULFONATES

The invention relates to a process for preparing polycyclic aromatic compounds by cross-coupling aromatic boron compounds with aromatic halogen compounds or perfluoroalkylsulfonates in a two-phase system under palladium catalysis in the presence of water-soluble complexing ligands.

The palladium-catalyzed cross-coupling reaction of aromatic boron compounds, such as boronic acids and their derivatives or boranes, and aromatic halogen compounds or perfluoroalkylsulfonates (see, for example, N. Miyaura, T. Yanagi, A. Suzuki in Synthetic Communications 11 (1981) 513; EP-A 0 470 795 and EP-A 0 354 434)) has been utilized for some years to an increasing degree in many fields of organic synthesis.

The cited processes are homogeneously catalyzed processes using Pd(0) complexes, in particular tetrakis (triphenylphosphine) palladium(0). The presence of phosphorus-containing complexing ligands generally considerably increases yields and selectivity of the reaction.

However, a disadvantage of these processes is, inter alia, the high catalyst costs which make difficult the economical transfer of the processes to a larger production scale (kg, t). In addition, contamination of the product and the waste with phosphorus compounds is observed, which can be a disadvantage particularly in the case of active compounds.

It is also known that water-soluble palladium couplings can be used for the abovementioned coupling reactions and that they can be carried out in pure aqueous or two-phase systems comprising organic and water phases (see, for example U.S. Pat. No. 5,043,510; J. P. Genet et al., Synlett 1992, 715). Here, water-soluble phosphine ligands such as triphenylphosphino-3,3', 3"-trisulfonate trisodium salt (TPPTS) are used to obtain the water-soluble palladium complex. However, it has been stated (A. L. Casalnuovo and J. C. Calabrese, J. Am. Chem. Soc. 112 (1990) 4324), that the yields in the two-phase system are significantly lower than in the single-phase system.

In addition, these processes suffer from the above described disadvantages of the catalyst costs and the contamination of the product with the complexing ligands.

Processes have been developed which reduce the catalyst costs by use of palladium metal as heterogeneous catalysts. However, the presence of a solid phase in the reaction mixture is not always desired.

It is therefore an object of the present invention to provide an economically favorable process for coupling aromatic boron compounds with aromatic perfluoroalkylsulfonates, which process gives the coupling products in very high purity and good yield, without the reaction having to be carried out in the presence of a solid phase.

It has now surprisingly been found that in the reaction of aromatic boron compounds such as boronic acids with aromatic halogen compounds or perfluoroalkylsulfonates in a two-phase reaction medium in the presence of a base, catalytic amounts of a palladium compound soluble in organic solvents and at least one water-soluble complexing ligand, polycyclic aromatic compounds are obtained in excellent yields and very high purities.

The invention accordingly provides a process for preparing polycyclic aromatic compounds by cross-coupling aromatic boron compounds with aromatic halogen compounds or perfluoroalkylsulfonates under palladium catalysis in the presence of at least one water-soluble complexing ligand, wherein the reaction medium forms an aqueous and an organic phase and the palladium is added in the form of a palladium compound soluble in the organic phase.

The reaction of the invention proceeds chemoselectively, so that even electrophilic groups such as esters or nitriles do not impair the course of the reaction.

The process of the invention allows polycyclic aromatic compounds to be prepared economically in very good yields and at the same time in very high purity, in particular without contamination by the complexing ligands.

The process of the invention is carried out in a multiphase system comprising an aqueous phase and an organic phase. The aqueous phase can here contain not only water but also one or more water-soluble organic solvents.

To carry out the process of the invention, the aromatic boron compound, the aromatic halogen compound or the perfluoroalkylsulfonate, the base, the catalytic amount of the palladium compound soluble in organic solvents and the water-soluble ligand are added to a mixture of water and one or more inert organic solvents and stirred at a temperature of from 0° C. to 200° C., preferably at from 30° C. to 170° C., particularly preferably at from 50° C. to 150° C., very particularly preferably at from 60° C. to 120° C., for a period of from 1 hour to 100 hours, preferably from 5 hours to 70 hours, particularly preferably from 5 hours to 50 hours.

The p rocess of the invention is preferably suitable for preparing products which are extractable from the aqueous into an organic phase.

The workup is carried out by known methods with which those skilled in the art are familiar.

To avoid contamination of the product with palladium, it is possible, for example, to add to the reaction mixture at the end of the reaction sufficient complexing ligand for all the palladium to be drawn into the aqueous phase. However, if desired, it is also possible after the reaction is complete to add a water-soluble complexing agent which is not identical to that used in the reaction, to transfer the palladium completely into the aqueous phase.

Naturally, the palladium can also, if desired, be removed by chromatographic methods or by precipitation, for example as sulfide.

The water-soluble, typically phosphorus-containing complexing ligand is completely removed from the product purely by separation of aqueous and organic phases.

For further workup after the phase separation, the crude product is usually freed of solvent and subsequently further purified by the method matched to the respective product, e.g. by recrystallization, distillation, sublimation, zone melting, melt crystallization or chroma-tography.

Organic solvents suitable for the process of the invention, which form an organic phase in the reaction medium, are, for example, ethers such as diethyl ether, dimethoxymethane, diethylene glycol dimethyl ether, diisopropyl ether, tert-butyl methyl ether, hydrocarbons such as hexane, isohexane, heptane, cyclohexane, benzene, toluene, xylene, higher alcohols not completely miscible with water such as 1-butanol, 2-butanol, tert-butanol, amyl alcohol, ketones such as isobutyl methyl ketone, amides such as dimethylacetamide, N-methylpyrrolidone, nitrites such as butyronitrile, and mixtures thereof.

Preferred organic solvents are ethers such as diethyl ether, dimethoxyethane, diethylene glycol dimethyl ether, diisopropyl ether, hydrocarbons such as hexane, heptane, cyclohexane, benzene, toluene, xylene, alcohols such as 1-butanol, 2-butanol, tert-butanol, ketones such as isobutyl methyl ketone, amides such as N-methylpyrrolidone, and mixtures thereof.

Particularly preferred solvents are hydrocarbons, e.g. cyclohexane, benzene, toluene, xylene and mixtures thereof.

In a particularly preferred variant, water, one or more water-insoluble and one or more water-soluble solvents are used in the process of the invention.

Preferred organic cosolvents miscible with the aqueous phase are nitriles such as acetonitrile, formamides such as DMF, lower alcohols such as methanol and ethanol, sulfoxides such as DMSO, and cyclic ether such as THF or dioxane.

Preferred reaction media comprising water, water-soluble organic solvent and water-insoluble organic solvent are mixtures of water, toluene and ethanol, water, toluene and tetrahydrofuran and water, toluene and acetonitrile, preferably in a volume ratio of 1:2:1 in each case.

Bases which are usually used in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alcoholates, and also primary, secondary and tertiary amines.

Particular preference is given to alkali metal and alkaline earth metal hydroxides, alkali metal and alkaline earth metal carbonates and alkali metal hydrogen carbonates.

Very particular preference is given to alkali metal hydroxides such as sodium hydroxide and potassium hydroxide, and also alkali metal carbonates and alkali metal hydrogen carbonates such as lithium carbonate, sodium carbonate and potassium carbonate.

In the process of the invention, the base is preferably used in a proportion of from 100 to 1,000 mol %, particularly preferably from 100 to 500 mol %, very particularly preferably from 150 to 400 mol %, most preferably from 180 to 250 mol %, based on the aromatic boron compound.

Catalysts used are palladium compounds soluble in organic solvents, such as palladium ketonates, palladium acetylacetonates, (nitrile)palladium halides, (olefin) palladium halides, palladium halides, allylpalladium halides and palladium biscarboxylates, preferably palladium ketonates, palladium acetylacetonates, bis($\eta^2$-olefin) palladium dihalides, palladium(II) halides, $\eta^3$-allylpalladium halide diners and palladium biscarboxylates, very particularly preferably bis (dibenzylideneacetone)palladium(0) [Pd(dba)$_2$], Pd(dba)$_2$. CHCl$_3$, palladiumbisacetylacetonate, bis(benzonitrile) palladium dichloride, PdCl$_2$, Na$_2$PdCl$_4$1 dichlorobis (dimethyl sulfoxide)palladium(II), bis(acetonitrile) palladium dichloride, palladium(II) acetate, palladium(II) propionate, palladium(II) butanoate and (1c,5c-cyclooctadiene)palladium dichloride.

The palladium catalyst is used in the process of the invention in a proportion of from 0.001 to 10 mol %, preferably 0.01 to 5 mol %, particularly preferably from 0.05 to 3 mol %, very particularly preferably from 0.1 to 1.5 mol %, based on the aromatic halogen compound or the perfluroalkylsulfonate.

Water-soluble ligands suitable for the process of the invention contain, for example, sulfonic acid salt radicals and/or sulfonic acid radicals and/or carbonic acid salt radicals and/or carbonic acid radicals and/or phosphonic acid salt and/or phosphonic acid radicals and/or phosphonium groups and/or peralkylammonium groups and/or hydroxy groups and/or polyether groups having an appropriate chain length.

Preferred classes of water-soluble ligands are the following types of compound substituted by the above groups: phosphines such as trialkylphosphines, tricycloalkylphosphines, triarylphosphines, dialkylarylphosphines, alkyldiarylphosphines and heteroarylphosphines such as tripyridylphosphine and trifurylphosphine, where the three substituents on the phosphorus can be identical or different, chiral or achiral and where one or more of the ligands can link the phosphorus groups of a plurality of phosphines and where a part of this linkage can also be one or more metal atoms, phosphites, phosphinous esters and phosphinous esters, phosphols, dibenzophosphols and cyclic or oligocyclic and polycyclic compounds containing phosphorus atoms.

Further suitable groups of water-soluble complexing ligands include, for example, bipyridines, phenanthrolines, porphyrins and alizarins which are modified with the above-mentioned groups.

Water-soluble phosphines preferably used are those of the formulae (I) to (VII),

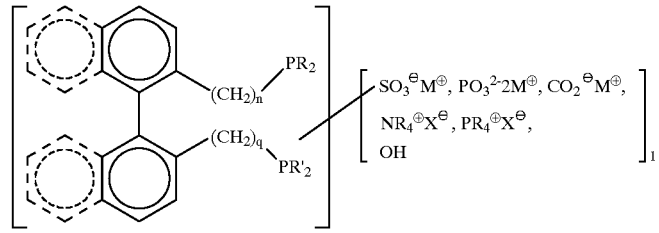

(I)

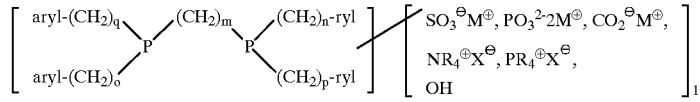

(II)

(III)
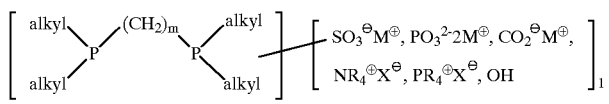

(IV)
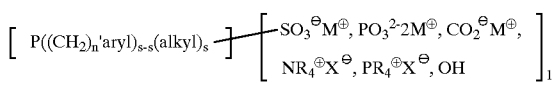

(V)
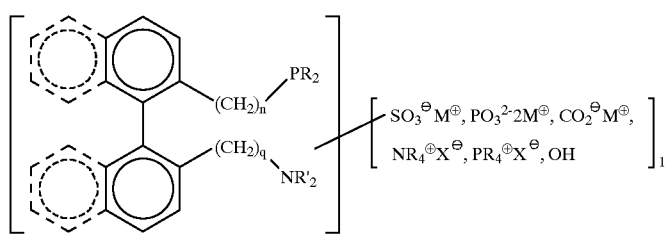

(VI)
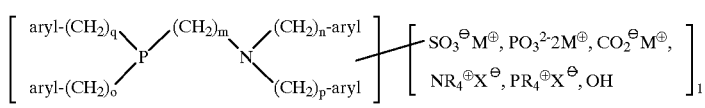

(VII)
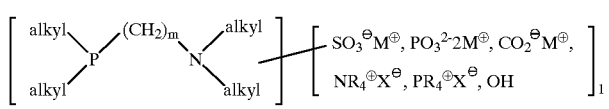

where the symbols and indices have the following meanings:

Aryl: a phenyl or naphthyl group which can also bear one or more substituents R;

Alkyl: a straight-chain or branched alkyl group having from 1 to 8 carbon atoms;

R,R': alkyl, aryl or aralkyl having from 1 to 18 carbon atoms;

M: alkali metal, alkaline earth metal or $NR_4$;

X: halogen, $BF_4$, $PF_6$, $OSO_2CF_3$, ½[$SO_4$];

l,m: 1 to 8;

n,o,p,q: 0.1 to 8;

s: 0.1 to 3.

Examples of particularly preferred water-soluble complexing ligands are shown below:
(Here, R is, unless indicated otherwise, as defined for the formulae (I) to (VII))

1. Sulfonated phosphines

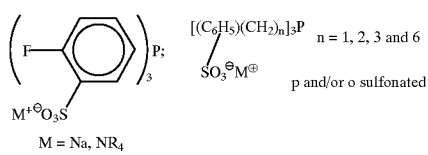

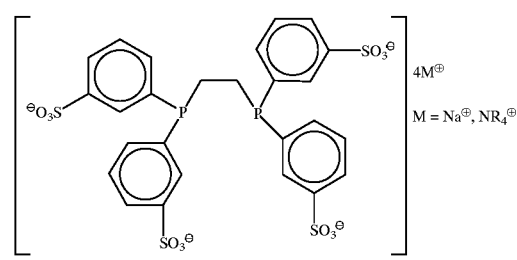

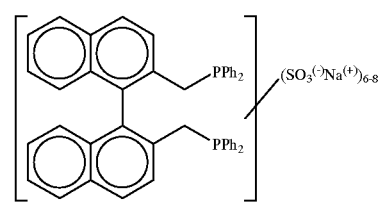

BINAS

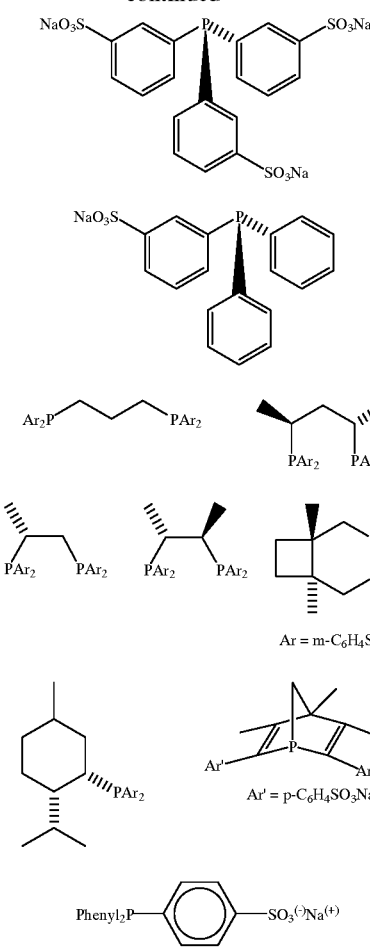

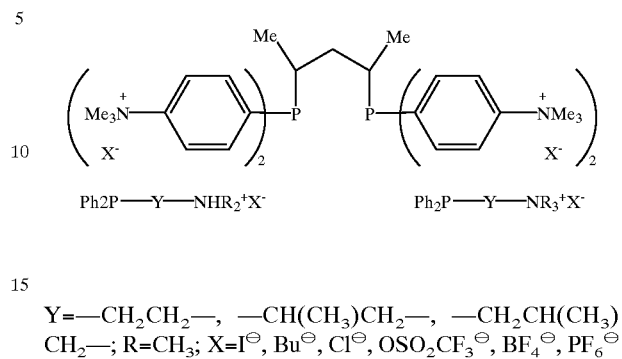

Y=—CH$_2$CH$_2$—, —CH(CH$_3$)CH$_2$—, —CH$_2$CH(CH$_3$)CH$_2$—; R=CH$_3$; X=I$^\ominus$, Bu$^\ominus$, Cl$^\ominus$, OSO$_2$CF$_3^\ominus$, BF$_4^\ominus$, PF$_6^\ominus$ 3. Carboxylated phosphines

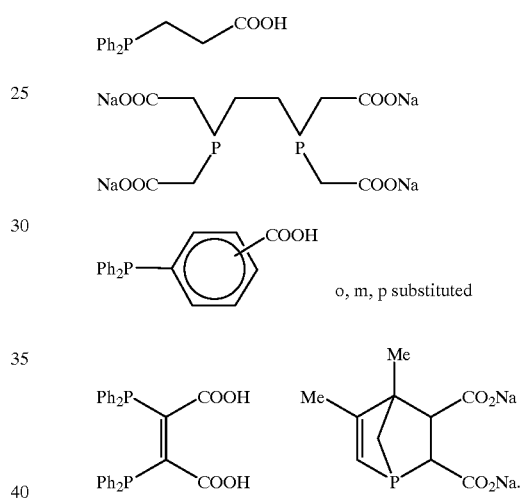

$R_{3-n}P(p\text{-}c_6H_4SO_3K)_n$  R=C$_6$H$_5$, 2-pyridyl, 3-pyridyl; n=1–3
P[p-OC$_6$H$_4$SO$_3$(NH(i-octyl)$_3$)]$_3$ 1.1 Phosphines having hydrophilic groups in the periphery

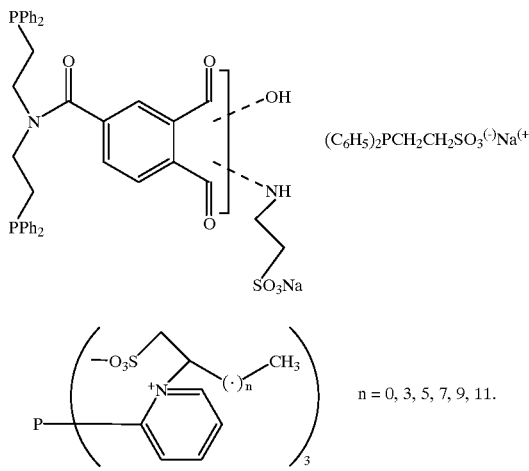

2. Phosphines having quaternized aminoalkyl and aminoaryl substituents

4. Phosphates having hydroxyalkyl or polyether substituents

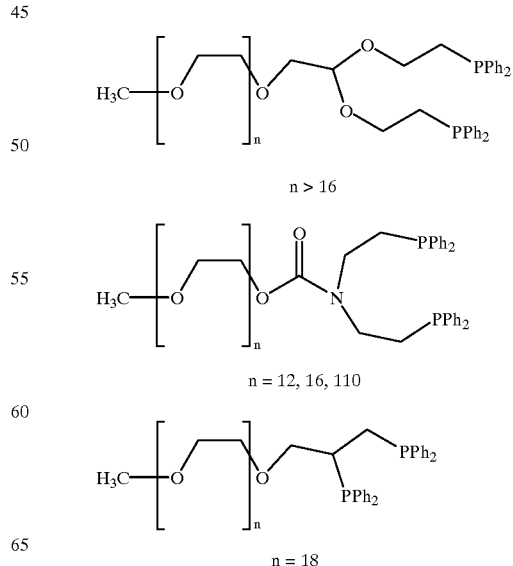

-continued

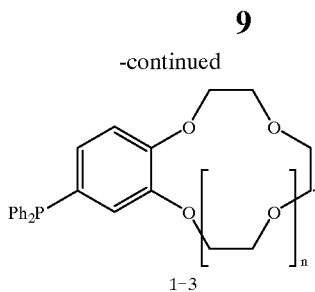

5. Phosphinoalkylphosphonium salts

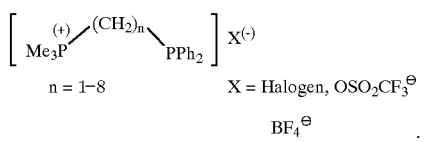

n = 1–8    X = Halogen, $OSO_2CF_3^{\ominus}$
$BF_4^{\ominus}$

6. Phosphites

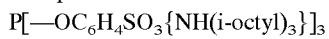

Very particularly preferred water-soluble phosphine ligands are:

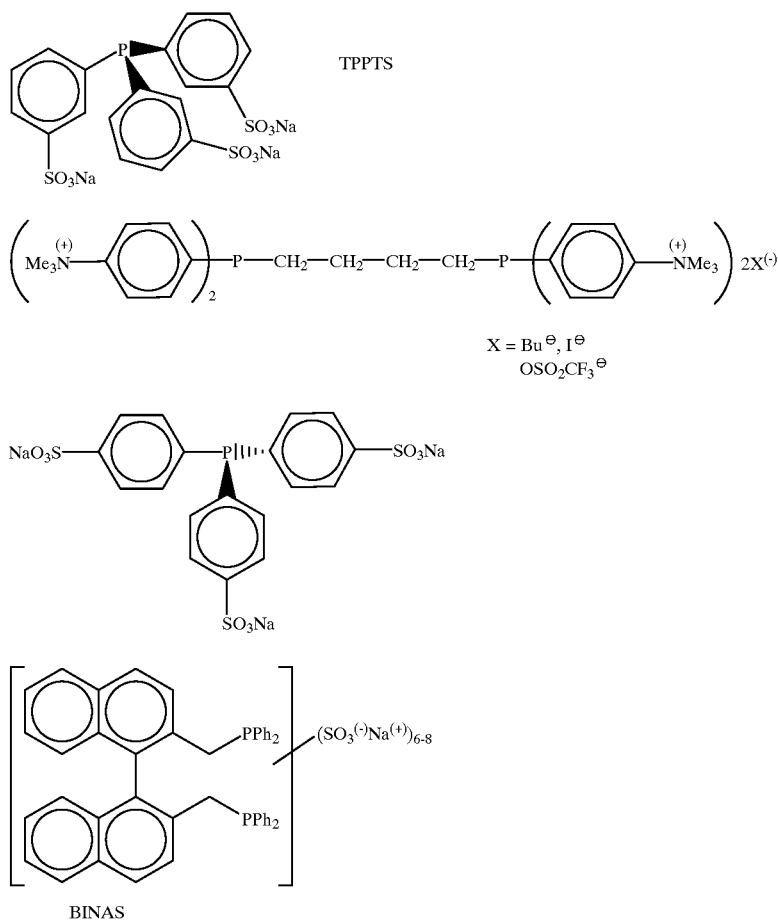

The water-soluble ligand is used in the process of the invention in a proportion of from 0.001 to 20 mol %, preferably from 0.01 to 15 mol %, particularly preferably from 0.05 to 10 mol %, very particularly preferably from 0.1 to 6 mol %, based on the aromatic halogen compound or the perfluoroalkylsulfonate.

If desired, mixtures of two or more different water-soluble complexing ligands can also be used.

The water-soluble complexing ligands used according to the invention are largely known from the literature. The syntheses of these compounds are described, for example, in W. A. Herrmann and C. W. Kohlpainter, Angew. Chem. Int. Ed. Engl. 32 (1993) 1524 and the literature cited therein or can be carried out by methods known from the literature or similar meth ods with which those skilled in the art are familiar. The preparation of BINAS is described, for example, in the German Patent Application P 42 44 274.

Starting compounds for the process of the invention are, on the on e hand, aromatic boron compounds of the formula (VIII), $$\text{Aryl-BQ}_1\text{Q}_2 \qquad (\text{VIII})$$

where
Aryl is an aromatic radical and
$Q_1$, $Q_2$ are identical or different and are —OH, $C_1$–$C_4$-alkoxy, $C_1$–$C_4$-alkyl, phenyl which may be unsubstituted or substituted by $C_1$–$C_4$-alkyl, $C_1$–$C_4$-alkoxy or halogen, or are halogen, or $Q_1$ and $Q_2$ together form a $C_1$–$C_4$-alkylenedioxy group, a methylene group which may be unsubstituted or substituted by one or two $C_1$–$C_4$-alkyl groups, or $Q_1$ and $Q_2$ and the boron atom together are part of a boroxine ring of the formula (IX):

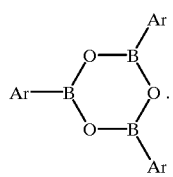
(IX)

Preference is given to aromatic boron compounds of the formula (X),

(X)

where $R^1$, $A^1$, $A^2$, $M^1$, $Q_1$, $Q_2$, k and l have the following meanings:

$R^1$ is benzyloxy, H, F, Cl, Br, —NC, —CN, —CF$_3$, —OCF$_3$ or a straight-chain, branched (with or without an asymmetric carbon atom) or a cyclic alkyl radical having from 1 to 18 carbon atoms, where one or two nonadjacent —CH$_2$-groups can also be replaced by —O—, —S—, —CO—, —CO—O—, —O—CO—, —CO—S, —S—CO—, —O—CO—O—, —CH=CH—, —C≡C—, —SO2—, —CON(H, C$_1$-C$_8$-alkyl)—, cyclopropane-1,2-diyl or —Si(CH$_3$)$_2$—, and where one or more hydrogen atoms of the alkyl radical can be replaced by F, Cl, Br or CN;

$A^1$ is 1,4-phenylene, pyrazine-2,5-diyl, pyridazine-3,6-diyl, pyridine-2,5-diyl, pyrimidine-2,5-diyl, trans-1,4-cyclohexylene, naphthalene-2,6-diyl, where one or more hydrogen atoms can be replaced by identical or different substituents L, where has one of the meanings given under $R^1$ or is 4,4-dimethylisoxazoline, and where one or two nonadjacent —CH$_2$ groups of the cyclohexylene can be replaced by —O— or —S—, or is 1,3,4-thiadiazole-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, piperidine-1,4-diyl, bicyclo-[2.2.2]octane-1,4-diyl, 1,3-dioxaborinane-2,5-diyl or trans-decalin-2,6-diyl;

$A^2$ is 1,4-phenylene, pyrazine-2,5-diyl, pyridazine-3,6-diyl, pyridine-2,5-diyl, pyrimidine-2,5-diyl, naphthalene-2,6-diyl, where one or more hydrogen atoms can be replaced by identical or different substituents L, where L has one of the meanings given under $R^1$ or is 4,4-dimethylisoxazoline, 1,3,4-thiadiazol-2,5-diyl, 1,3-thiazol-2,4-diyl, 1,3-thiazol-2,5-diyl, thiophene-2,4-diyl or thiophene-2,5-diyl;

$M^1$ is —O—, —S—, —CO—, —CO—O—, O—CO—, —CO—S, —S—CO—, —O—CO—O—, —CH$_2$—O—, —OCH$_2$—, —CH$_2$CH$_2$—, —CH=CH—, —C≡C—, —CH(CN)—CH$_2$—, —CH$_2$—CH(CN)—, —CH=N—, —N=CH—, —CH$_2$CH$_2$CH$_2$—O—, —OCH$_2$CH$_2$CH$_2$—, —CH$_2$CH$_2$CO—O—, —O—COCH$_2$CH$_2$—, and $Q_1$, $Q_2$ are identical or different and are —OH, C$_1$-C$_4$-alkoxy or halogen, or $Q_1$ and $Q_2$ together form a C$_1$-C$_4$-alkylenedioxy group or $Q_1$ and $Q_2$ and the boron atom together are part of a boroxine ring of the formula (IX):

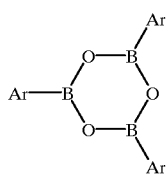
(IX)

k, l are, independently of one another, zero or one.

$R^1$ is preferably benzyloxy, H, F, Cl, —CF$_3$, OCF$_3$, CN or a straight-chain, branched (with or without an asymmetric carbon atom) or cyclic alkyl radical having from 1 to 18 carbon atoms, where one or two nonadjacent —CH$_2$—groups can also be replaced by —O—, —CO—, —CO—O—, —OCO—, —O—CO—O—, —CH=CH—, —C≡C—, cyclopropane-1,2-diyl or—Si(CH$_3$)$_2$—, and where one or more hydrogen atoms of the alkyl radical can also be replaced by F, Cl or CN.

$R^1$ is particularly preferably benzyloxy, H or a straight-chain, branched (with or without an asymmetric carbon atom) or cyclic alkyl radical having from 1 to 18 carbon atoms, where one or two nonadjacent —CH$_2$ groups can also be replaced by —O—, —CH=CH—, —C≡C—, cyclopropane-1,2-diyl or —Si(CH$_3$)$_2$—.

$A^1$ is preferably 1,4-phenylene, pyrazine-2,5-diyl, pyridazine-3,6-diyl, naphthalene-2,6-diyl, pyridine-2,5-diyl, pyrimidine-2,5-diyl, where one or more hydrogen atoms can be replaced by identical or different substituents L, where L has one of the meanings given under $R^1$, or trans-1,4-cyclohexylene, where one or two nonadjacent —CH$_2$ groups can be replaced by —O—, or 1,3,4-thiadiazol-2,5-diyl, or bicyclo[2.2.2]octane-1,4-diyl.

$A^1$ is particularly preferably 1,4-phenylene, 2-fluoro-1,4-phenylene, 1,4-phenylene, 2,3-difluoro-1,4-phenylene, 2,6-difluoro-1,4-phenylene, 2,5-difluoro-1,4-phenylene, or pyridine-2,5-diyl, pyrimidine-2,5-dyil, where one or two hydrogen atoms can be replaced by identical or different substituents L where L has one of the meanings given under $R^1$, or trans-1,4-cyclohexylene.

$A^2$ is preferably 1,4-phenylene, pyrazine-2,5-diyl, pyridazine-3,6-diyl, pyridine-2,5-diyl, pyrimidine-2,5-diyl, naphthalene-2,6-diyl, where one or more hydrogen atoms can be replaced by identical or different substituents L, where L has one of the meanings given under $R^1$.

$A^2$ is particularly preferably 1,4-phenylene, 2-fluoro-1,4-phenylene, 2,3-difluoro-1,4-phenylene, 2,6-difluoro-1,4-phenylene, 2,5-difluoro-1,4-phenylene, or pyridine-2,5-diyl, or naphthalene-2,6-diyl, where one or more hydrogen atoms can be replaced by identical or different substituents L, where L has one of the meanings given under $R^1$.

$M^1$ is preferably —O—, —CO—, —CO—O—, —O—CO—, —O——CO—O—, —CH$_2$—O—, —O—CH$_2$—, —CH$_2$—CH$_2$—, —CH=CH—, —C≡C—, —CH$_2$CH$_2$CH$_2$—O—, —O—CH$_2$CH$_2$CH$_2$—, —CH$_2$CH$_2$CO—O— or —O—CO—CH$_2$CH$_2$—, $M^1$ is particularly preferably —O—, —CH$_2$—O—, —O—CH$_2$—, —CH$_2$CH$_2$—, —CH=CH— or —C≡C—.

Very particular preference is given to the aromatic boronic acids of the formulae (Xa) to (Xh) listed below:

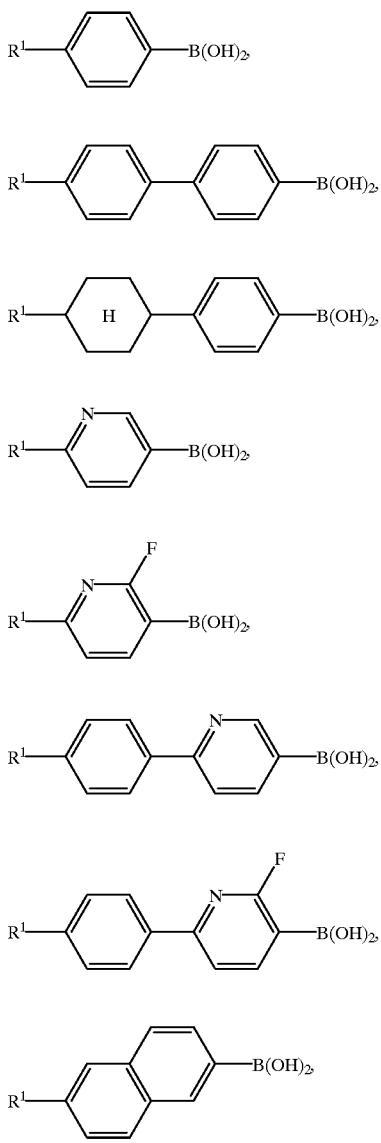

where $R^1$ is benzyloxy, H, methyl, ethyl, propyl, butyl, pentyl, hexyl, heptyl, octyl, nonyl, decyl, undecyl, dodecyl, tridecyl, tetradecyl and pentadecyl, or methoxy, ethoxy, propoxy, butoxy, pentoxy, hexoxoy, heptoxy, octoxy, nonoxy, decoxy, undecoxy, dodecoxy, tridecoxy, tetradecoxy or pentadecoxy.

The aromatic boron compounds used are either known or can be prepared by known methods as are described, for example, in Houben Weyl, Methoden der Organischen Chemie, Georg Thieme-Verlag, Stuttgart, Volume 13/3a . It is thus, for example, possible to obtain boronic acids, preferably those of the formula (VIII), from aromatic alkali metal and magnesium compounds by reaction with trialkoxyboranes and subsequent hydrolysis.

The second class of starting compounds for the process of the invention are aromatic halogen compounds or aromatic perfluoroalkylsulfonates, preferably those of the formula (XI),

where $R^2$, $A^3$, $A^4$, $M^2$, X, m and n have the following meanings:

$R^2$ is benzyloxy, H, F, Cl, Br, —NC, —CN, —CF$_3$, —OCF$_3$, isoxazoline or a straight-chain, branched (with or without an asymmetric carbon atom) or cyclic alkyl radical having from 1 to 18 carbon atoms, where one or two nonadjacent —CH$_2$—groups can also be replaced by —O—, —S—, —Co—, —CO—O—, —O—CO—, —CO—S—, —S—CO—, —O—CO—O—, —SO$_2$—, —CON(H,C$_1$-C$_8$-alkyl)—, —CH=CH—, —C≡C—, cyclopro-pane-1,2-diyl or —Si(CH$_3$)$_2$—, and where one or more hydrogen atoms of the alkyl radical can also be replaced by F, Cl, Br or CN;

$A^4$ is 1,4-phenylene, pyrazine-2,5-diyl, pyridazine-3,6-diyl, pyridine-2,5-diyl, pyrimidine-2,5-diyl, trans-1,4-cyclohexylene, naphthalene-2,6-diyl, where one or more hydrogen atoms can be replaced by identical or different substituents L, where L has one of the meanings given under $R^1$, or is —CHO or 4,4-dimethylisoxazoline, and where one or two nonadjacent —CH$_2$ groups of the cyclohexylene can be replaced by —O— or —S—, or is 1,3,4-thiadiazol-2,5-diyl, 1,3-thiazol-2,4-diyl, 1,3-thiazol- 2,5-diyl, thiophene-2,4-diyl, thiophene-2,5-diyl, piperazine-1,4-diyl, piperazine-2,5-diyl, piperidine-1,4-diyl, bicyclo [2.2.2]octane-1,4-diyl, 1,3-dioxaborinane-2,5-diyl or trans-decalin-2,6-diyl;

$A^3$ is 1,4-phenylene, pyrazine-2,5-diyl, pyridazine-3,6-diyl, pyridine-2,5-diyl, pyrimidine-2,5-diyl, naphthalene-2,6-diyl, where one or more hydrogen atoms can be replaced by identical or different substituents L where L has one of the meanings given under $R^1$ or is —CHO or 4,4-dimethylisoxazoline, or 1,3,4-thiadiazol-2,5-diyl, 1,3-thiazol-2,4-diyl, 1,3-thiazol-2,5-diyl, thiophene-2,4-diyl or thiophene-2,5-diyl;

$M^2$ is —O—, —S—, —CO—, —CO—O—, O—CO—, —CO—S, S—CO—, —O—CO—O—, —CH$_2$—O—, —OCH$_2$—, —CH$_2$CH$_2$—, —CH=CH—, —C≡C—, —CH(CN)—CH$_2$—, —CH$_2$—CH(CN)—, —CH=N—, —N=CH—, —CH$_2$CH$_2$CH$_2$—O—, —OCH$_2$CH$_2$CH$_2$—, —CH$_2$CH$_2$CO—O—, —O—COCH$_2$CH$_2$—;

X is Cl, Br, I or perfluoroalkylsulfonate; and m, n are, independently of one another, zero or one.

$R^2$ is preferably benzyloxy, H, F, Cl, Br, —CN, —CF$_3$, —OCF$_3$ or a straight-chain, branched (with or without an asymmetric carbon atom) or cyclic alkyl radical having from 1 to 18 carbon atoms, where one or two nonadjacent —CH$_2$-groups can also be replaced by —O—, —CO—, —CO—O—, —O—CO—, —O—CO—O—, —CH=CH—, —C≡C—, cyclopropane-1,2-diyl or —Si(CH$_3$)$_2$—, and where one or more hydrogen atoms of the alkyl radical can also be replaced by F, Cl or CN.

$R^2$ is particularly preferably benzyloxy, H, Cl, Br or a straight-chain, branched (with or without an asymmetric carbon atom) or cyclic alkyl radical having from 1 to 18 carbon atoms, where one or two nonadjacent —CH$_2$-groups can also be replaced by —O—, —CO—, —CO—O—, —O—, —O—CO—, —O—CO—O—, —CH=CH—, —C≡C—, cyclopropane-1,2-diyl or —Si(CH$_3$)—

$A^3$ is preferably 1,4-phenylene, pyrazine-2,5-diyl, pyridazine-3,6-diyl, pyridine-2,5-diyl, pyrimidine-2,5-diyl, naphthalene-2,6-diyl, where one or more hydrogen atoms can be replaced by identical or different substituents L, where L has one of the meanings given under $R^1$ or is —CHO or 4,4-dimethylisoxazoline, or 1,3,4-thiadiazol-2,5-diyl.

$A^3$ is particularly preferably 1,4-phenylene, 2-fluoro-1,4-phenylene, 2,3-difluoro-1,4-phenylene, 2,6-difluoro-1,4-phenylene, 2,5-difluoro-1,4-phenylene, or pyrazine-2,5-diyl, pyridazine-2,5-diyl, pyrimidine-2,5-diyl or naphthalene-2,6-diyl, where one or more hydrogen atoms can be replaced by identical or different substituents L, where L has one of the meanings given under $R^1$ or is —CHO or 4,4-dimethylisoxazoline.

$A^4$ is preferably 1,4-phenylene, pyrazine-2,5-diyl, pyridazine-3,6-diyl, pyridine-2,5-diyl, pyrimidine-2,5-diyl, trans-1,4-cyclohexylene, naphthalene-2,6-diyl where one or more hydrogen atoms can be replaced by identical or different substituents L, where L has one of the meanings given under $R^1$, and where one or two nonadjacent —$CH_2$ groups of the cyclohexylene can be replaced by —O—, or 1,3,4-thiadiazol-2,5-diyl or bicyclo [2.2.2]octane-1,4-diyl.

$A^4$ is particularly preferably 1,4-phenylene, 2-fluoro-1,4-phenylene, 2,3-difluoro-1,4-phenylene, 2,6-difluoro-1,4-phenylene, 2,5-difluoro-1,4-phenylene, or pyridine-2,5-diyl, pyrimidine-2,5-diyl, trans-1,4-cyclohexylene, naphthalene-2,6-diyl, where one or more hydrogen atoms can be replaced by identical or different substituents L, where L has one of the meanings given under $R^1$.

$M^2$ is preferably —O—, —CO—, —CO—O—, —O—CO—, —O—CO—O—, —$CH_2$—O—, —O—$CH_2$—, —$CH_2CH_2$—, —CH=CH—, —C≡C—, —$CH_2CH_2CH_2$—O—, —O—$CH_2CH_2CH_2$—, —$CH_2CH_2$CO—O— or —O—CO—$CH_2CH_2$.

$M^2$ is particularly preferably —O—, —CO—, —CO—O—, —O—CO—, —O—CO—O—, —$CH_2$—O—, —O—$CH_2$—, —$CH_2CH_2$—, —CH=CH—, —C≡C—, —$CH_2CH_2CH_2$—O—, —O—$CH_2CH_2CH_2$—, —$CH_2CH_2$CO—O— or —O—CO—$CH_2$, $CH_2$.

X is preferably bromine, iodine or $OSO_2$-$C_pF_{2p+1}$, where p has an integral value from 1 to 10. X is particularly preferably bromine.

Very particular preference is given to the aromatic halogen compounds of the formulae (XI 1) to (XI 31) listed below:

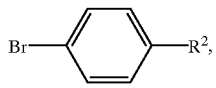
XI 1

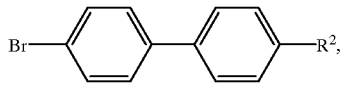
XI 2

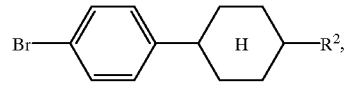
XI 3

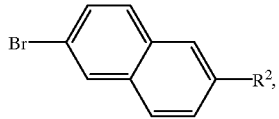
XI 4

-continued

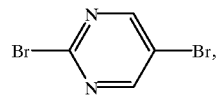
XI 5

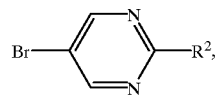
XI 6

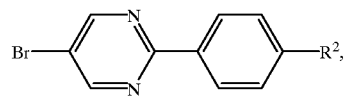
XI 7

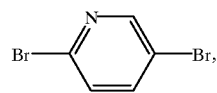
XI 8

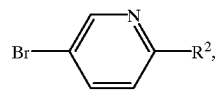
XI 9

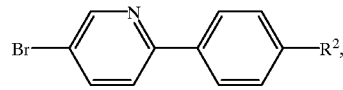
XI 10

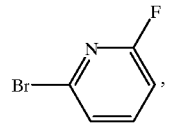
XI 11

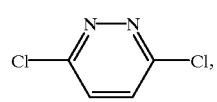
XI 12

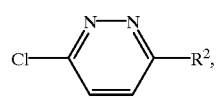
XI 13

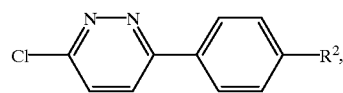
XI 14

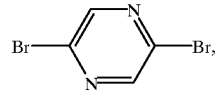
XI 15

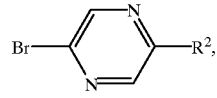
XI 16

XI 17 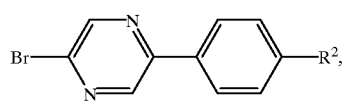

XI 18 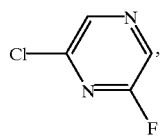

XI 19 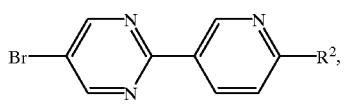

XI 20 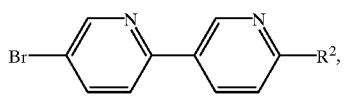

XI 21 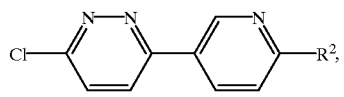

XI 22 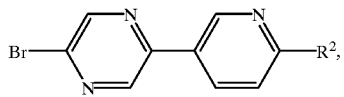

XI 23 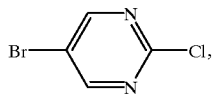

XI 24 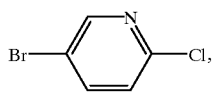

XI 25 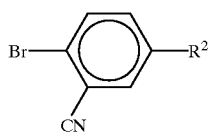

XI 26 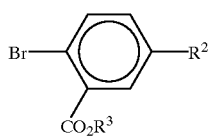

XI 27 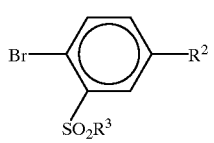

XI 28 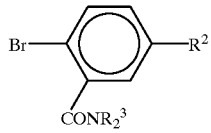

XI 29 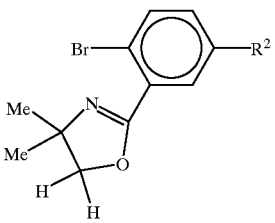

XI 30 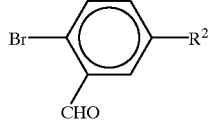

XI 31 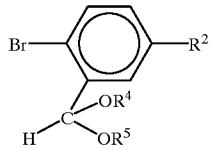

XI 32 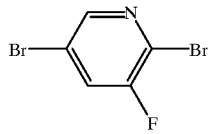

XI 33 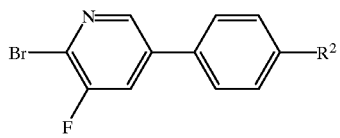

XI 34 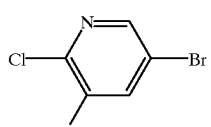

XI 35 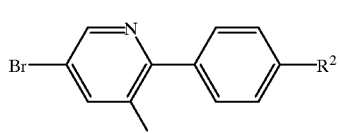

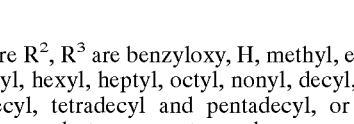

where $R^2$, $R^3$ are benzyloxy, H, methyl, ethyl, propyl, butyl, pentyl, hexyl, heptyl, octyl, nonyl, decyl, undecyl, dodecyl, tridecyl, tetradecyl and pentadecyl, or methoxy, ethoxy, propoxy, butoxy, pentoxy, hexoxoy, heptoxy, octoxy, nonoxy, decoxy, undecoxy, dodecoxy, tridecoxy, tetradecoxy or pentadecoxy and $R^4$, $R^5$ are methyl, ethyl, propyl, butyl, pentyl, hexyl, heptyl, octyl, nonyl, decyl, undecyl, tridecyl, tetradecyl or pentadecyl, or R4 and $R^5$ together are —$(CH_2)_2$— or —$(CH_2)_3$—.

The aromatic halogen compounds and perfluoroalkyl-sulfonates used are either known or can be prepared by known methods as are described, for example, in Houben Weyl, Methoden der Organischen Chemie, Georg ThiemeVerlag, Stuttgart, Volume 5/3 and 5/4. For example, aromatic halides can be obtained by replacing the diazonium group in a corresponding diazonium salt by chlorine, bromine or iodine.

Furthermore, hydroxy-substituted nitrogen heterocycles can be converted into the corresponding halides by means of phosphorus trihalides and phosphorus oxytrihalides. The process of the invention for cross-coupling aromatic boron compounds with aromatic halogen compounds or perfluoroalkylsulfonates can likewise be used for preparing compounds of the formula (XI). Perfluoroalkyl-sulfonates of the formula (XI), where X is $OSO_2$-$C_nH_{2n+1}$, can be prepared by esterification of corresponding alcohols of the formula (III), where X is a hydroxyl group, with perfluoroalkanesulfonic acids or their reactive derivatives. The corresponding perfluoroalkanesulfonic acids are known. Suitable reactive derivatives of the specified perfluoroalkanesulfonic acids are, in particular, the acid halides, especially the chlorides and bromides, and also the anhydrides.

Products of the process of the invention are polycyclic aromatic compounds.

Preferred products formed in the process of the invention are compounds of the formula (XII), $$R^1(-A^1)_k(-M^1)_l-A^2-A^3(-M^2)_M(-A^4)_n-R^2 \qquad (XII)$$

where $R^1$ and $R^2$ can be, independently of one another, benzyloxy, H, F, Cl, Br, —NC, —CN, —$CF_3$, —$OCF_3$ or a straight-chain, branched (with or without an asymmetric carbon atom) or cyclic alkyl radical having from 1 to 18 carbon atoms, where one or two nonadjacent —$CH_2$-groups can also be replaced by —O—, —S—, —CO—, —CO—O—, —O—CO—, —CO—S—, —S—CO—, —O—CO—O—, —CH═CH—, —C≡C—, —$SO_2$—, $CON(H,C_1$-$C_8$-alkyl), cyclopropane-1,2-diyl or —$Si(CH_3)_2$— and where one or more hydrogen atoms of the alkyl radical can also be replaced by F, Cl, Br or CN;

$A^1$ and $A^4$ can each be, independently of one another, 1,4-phenylene, pyrazine-2,5-diyl, pyridazine-3,6-diyl, pyridine-2,5-diyl, pyrimidine-2,5-diyl, trans-1,4-cyclohexylene, naphthalene-2,6-diyl, where one or more hydrogen atoms can be replaced by identical or different substituents L, where L has one of the meanings given under $R^1$ or is 4,4-dimethylisoxazoline, and where one or two nonadjacent —$CH_2$ groups of the cyclohexylenes can be replaced by —O— or —S—, or 1,3,4-thiadiazol-2,5-diyl, 1,3-thiazol-2,4-diyl, 1,3-thiazol-2,5-diyl, thiophene-2,4-diyl, thiophene-2,5-diyl, piperazine-1,4-diyl, piperazine-2,5-diyl, piperidine-1,4-diyl, bicyclo[2.2.21]-octane-1,4-diyl, 1,3-dioxaborinane-2,5-diyl or transdecalin-2,6-diyl;

$A^2$ and $A^3$ are each, independently of one another, 1,4-phenylene, pyrazine-2,5-diyl, pyridazine-3,6-diyl, pyridine-2,5-diyl, pyrimidine-2,5-diyl, naphthalene-2,6-diyl, where one or more hydrogen atoms can be replaced by identical or different substituents L, where L has one of the meanings given under $R^1$, is 4,4-dimethylisoxazoline or, in the case of $A^3$, also —CHO, or 1,3,4-thiadiazol-2,5-diyl, 1,3-thiazol-2,4-diyl, 1,3-thiazol-2,5-diyl, thiophene-2,4-diyl or thiophene-2,5-diyl;

$M^1$ and $M^2$ can each be, independently of one another, —O—, —S—, —CO—, —CO—O—, —O—CO—, —CO—S—, —S—CO—, —O—CO—O—, —$CH_2$—O—, —O$CH_2$—, —$CH_2CH_2$—, —CH═CH—, —C≡C—, —CH(CN)—$CH_2$—, —$CH_2$—CH(CN)—, —CH═N—, —N═CH—, —$CH_2CH_2CH_2$—O—, —O$CH_2CH_2CH_2$—, —$CH_2CH_2$CO—O—, —O—CO$CH_2CH_2$—; and k, l, m, n are each, independently of one another, zero or one.

Preferred and particularly preferred variants of $R^1$, $R^2$, $A^1$, $A^2$, $A^3$, $A^4$, $M^1$, $M^2$, k, l, m, n are given in the formulae (II) and (III).

Very particular preference is given to the compounds of the formulae (XII 1) to (XII 101) listed below:

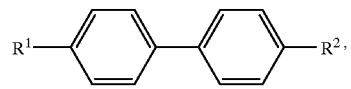

XII 1

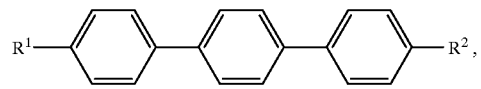

XII 2

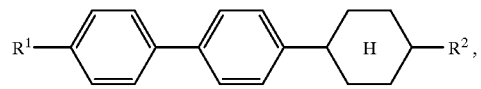

XII 3

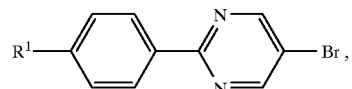

XII 4

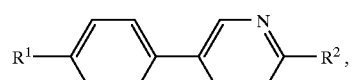

XII 5

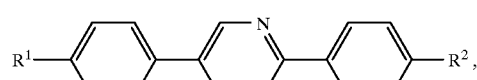

XII 6

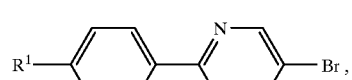

XII 7

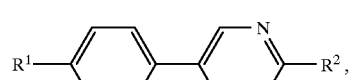

XII 8

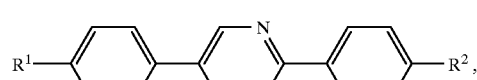

XII 9

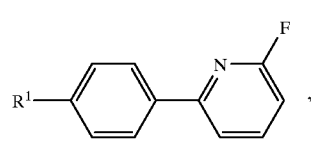

XII 10

XII 11
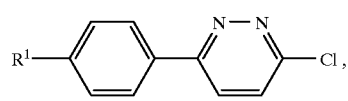
XII 12
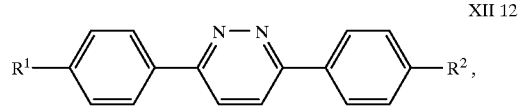
XII 13
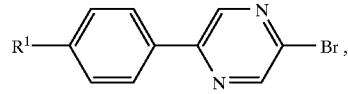
XII 14
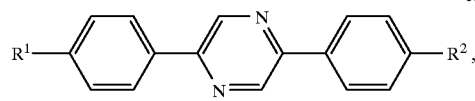
XII 15
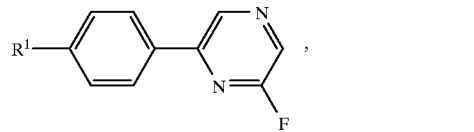
XII 16
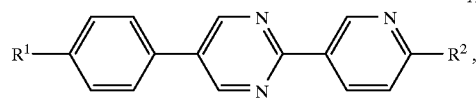
XII 17
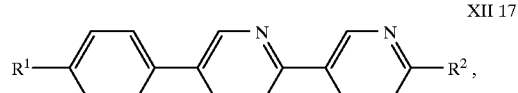
XII 18
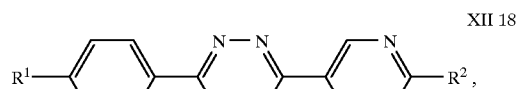
XII 19
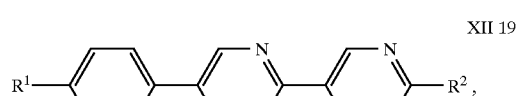
XII 20
XII 21
XII 22
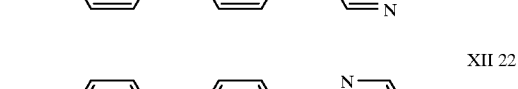
XII 23
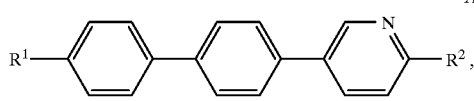
XII 24
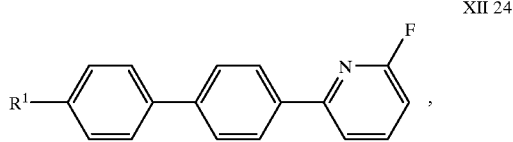
XII 25
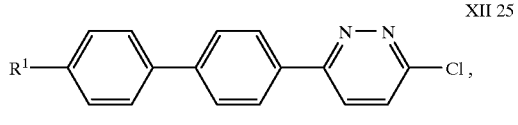
XII 26
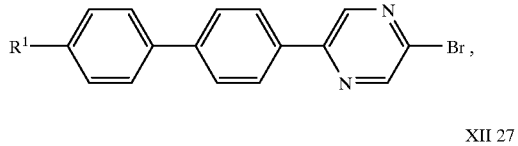
XII 27
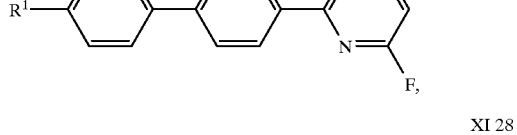
XI 28
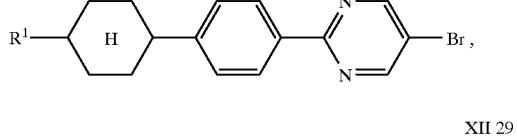
XII 29
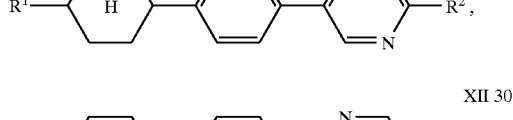
XII 30
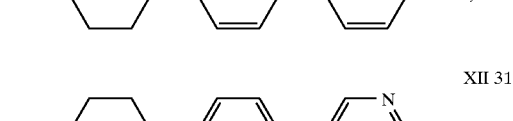
XII 31
XII 32
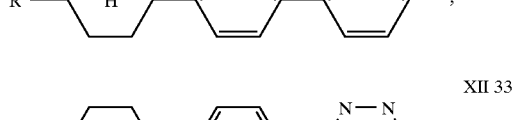
XII 33
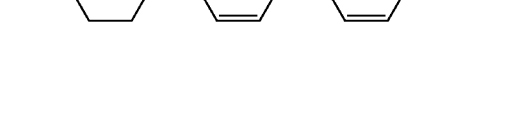

-continued
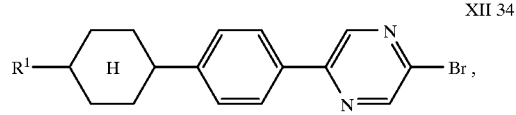 XII 34
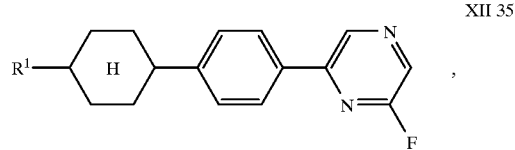 XII 35
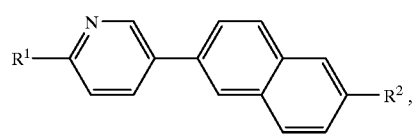 XII 36
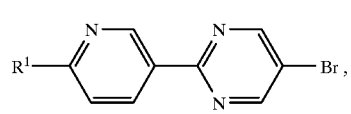 XII 37
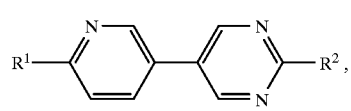 XII 38
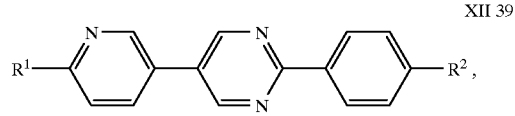 XII 39
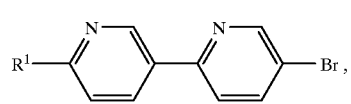 XII 40
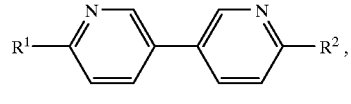 XII 41
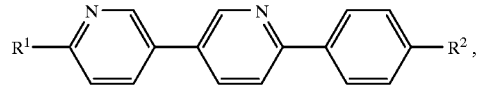 XII 42
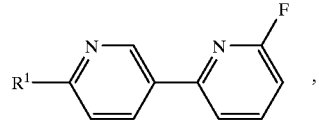 XII 43
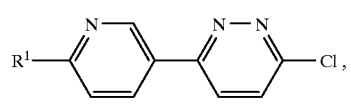 XII 44
-continued
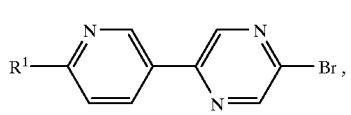 XII 45
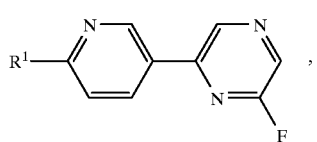 XII 46
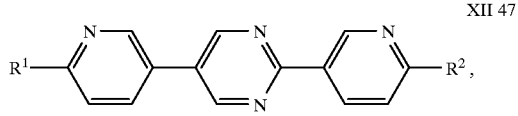 XII 47
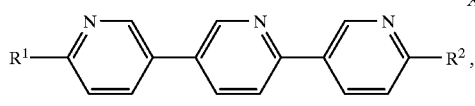 XII 48
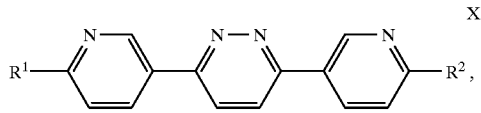 XII 49
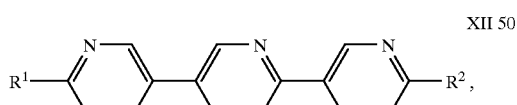 XII 50
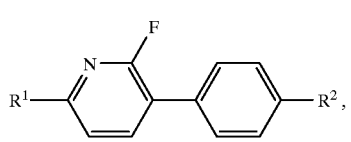 XII 51
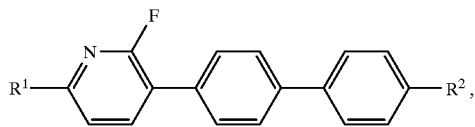 XII 52
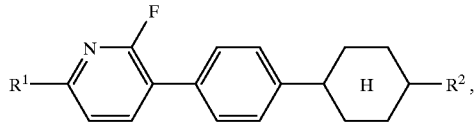 XII 53
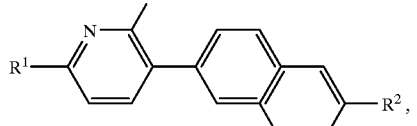 XII 54

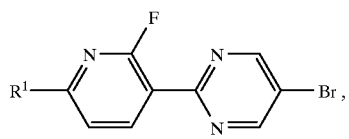
XII 55
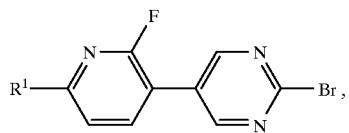
XII 56
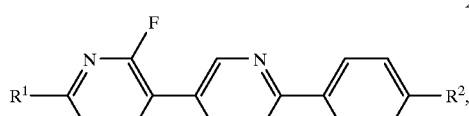
XII 57
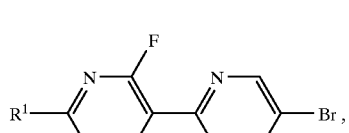
XII 58
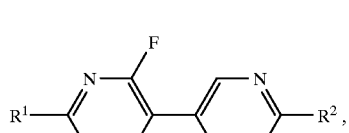
XII 59
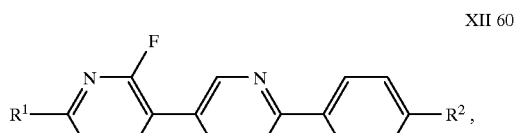
XII 60
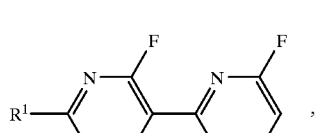
XII 61
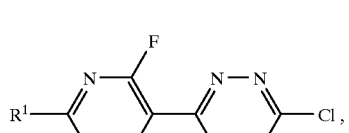
XII 62
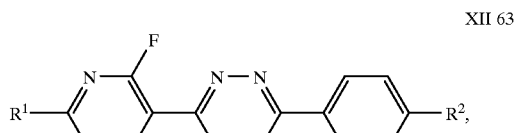
XII 63
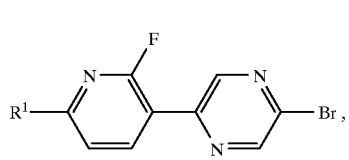
XII 64
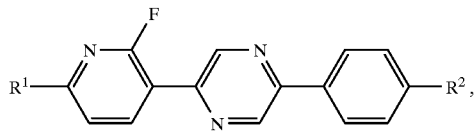
XII 65
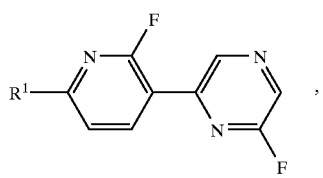
XII 66
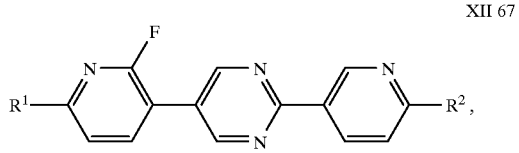
XII 67
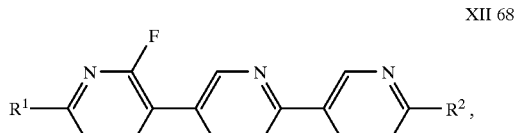
XII 68
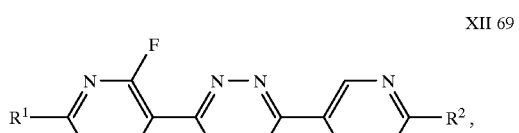
XII 69
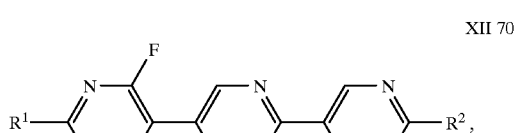
XII 70
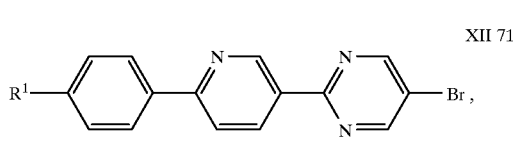
XII 71
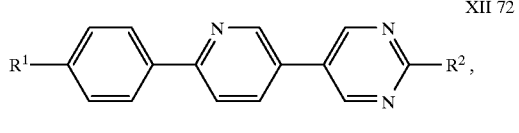
XII 72
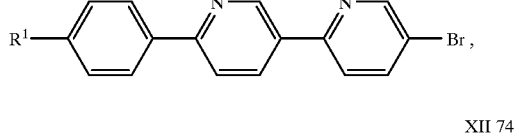
XII 73
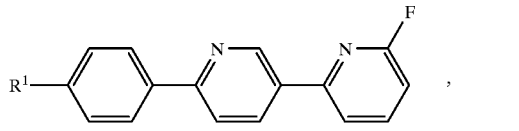
XII 74

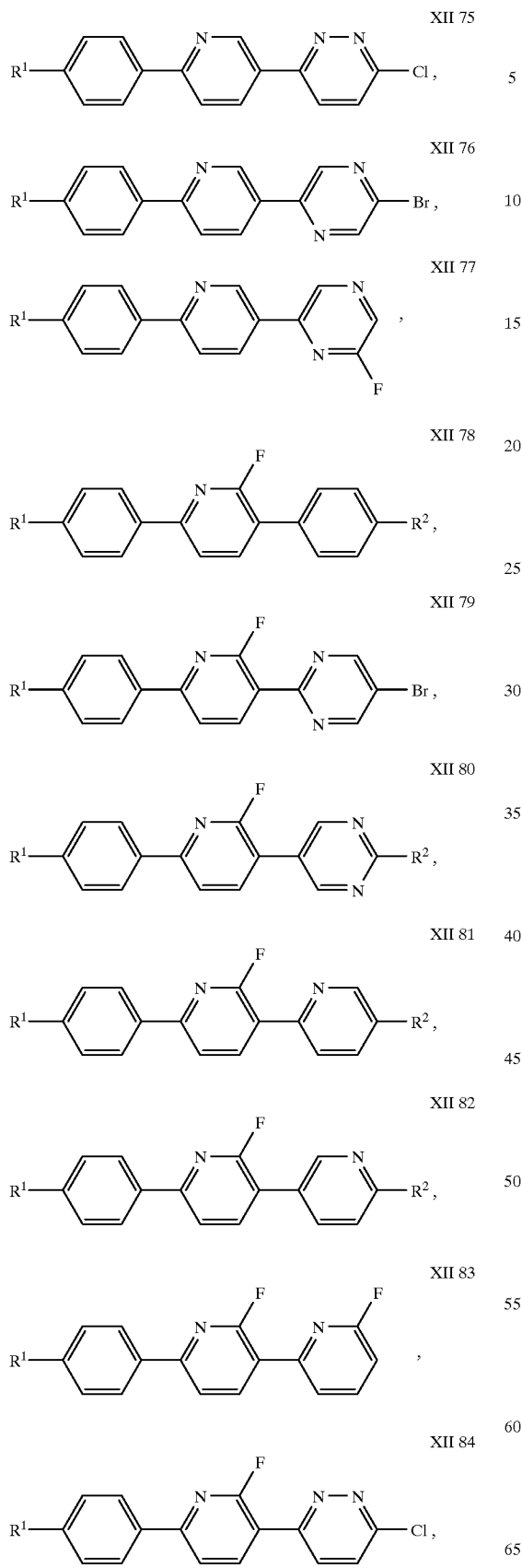
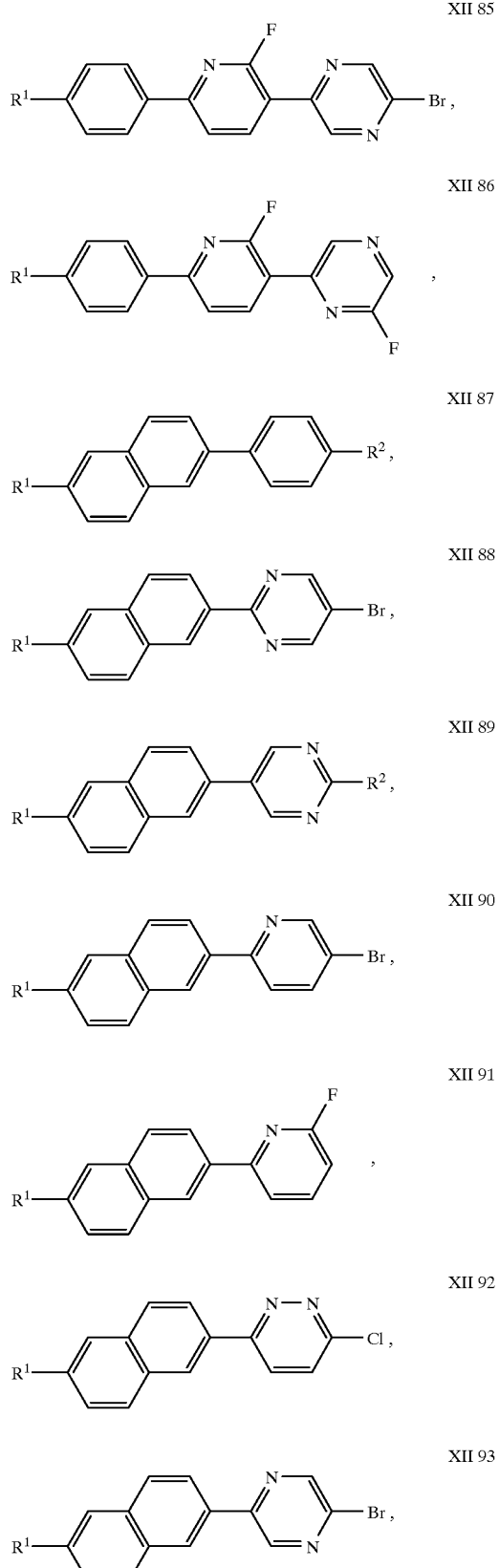

-continued

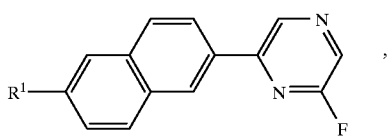 XII 94

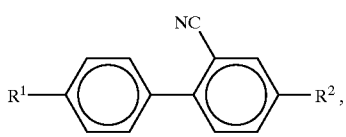 XII 95

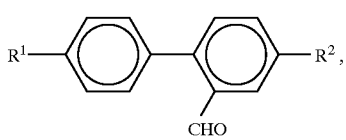 XII 96

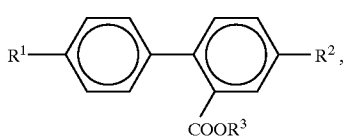 XII 97

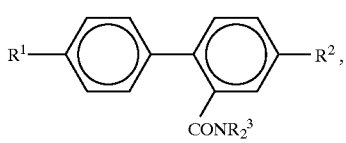 XII 98

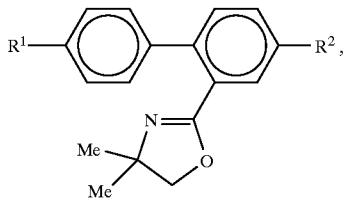 XII 99

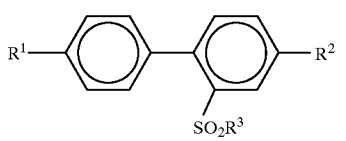 XII 100

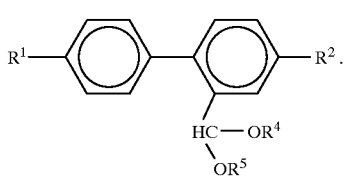 XII 101 where $R^1$, $R^2$ and $R^3$ are benzyloxy, H, methyl, ethyl, propyl, butyl, pentyl, hexyl, heptyl, octyl, nonyl, decyl, undecyl, dodecyl, tridecyl, tetradecyl and pentadecyl, or methoxy, ethoxy, propoxy, butoxy, pentoxy, hexoxy, heptoxy, octoxy, nonoxy, decoxy, undecoxy, dodecoxy, tridecoxy, tetradecoxy and pentadecoxy, $R^4$, $R^5$ are methyl, ethyl, propyl, butyl, pentyl, hexyl, heptyl, octyl, nonyl, decyl, undecyl, dodecyl, tridecyl, tetradecyl and pentadecyl or $R^4$ and $R^5$ together are —(CH$_2$)$_2$— or —(CH$_2$)$_3$—.

The compounds of the formula (XII) are suitable for use as liquid-crystalline materials or can be used as intermediates for the preparation of further liquidcrystalline compounds. Furthermore, the compounds of the formula (XII) are used as precursors for pharmaceuticals, cosmetics, fungicides, herbicides, insecticides, dyes, detergents and polymers, including as additives for the same.

Compounds prepared according to the invention as are represented by, for example, the formulae (XII 95) to (XII 100) are particularly valuable precursors for angiotensin II inhibitors (see, for example, Drugs of the Future, 18 (1993) 428–432).

The present invention is illustrated by the examples described below, without being limited thereby. The abbreviations used in the examples have the following meanings:

mp.=melting point
X=crystalline
S=smectic
$S_C$=smectic C
$S_A$=smectic A
N=nematic
I=isotropic

EXAMPLE 1

2-Bromobenzonitrile (3.1 g) and 2.75 g of 4-methylphenyl-boronic acid are dissolved in 20 ml of toluene and 10 ml of ethanol. The solution is admixed with 40.4 mg (1 mol %) of palladium(II) acetate and 4.74 g of sodium carbonate in 10 ml of water. 0.36 mmol of triphenylphosphino-3,3',3"-trisulfonate trisodium salt (TPPTS) are subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated off on a rotary evaporator. The residue is crystallized from 50 ml of n-heptane. Yield: 2.9 g of 4-methyl-2'-cyanobiphenyl, melting point 49° C.

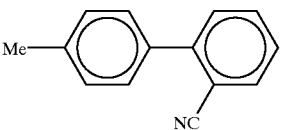

EXAMPLE 2

2-Bromobenzonitrile (3.1 g) and 2.75 g of 4-methylphenyl-boronic acid are dissolved in 20 ml of toluene and 10 ml of ethanol. The solution is admixed with 4 mg (0.1 mol %) of palladium(II) acetate and 4.47 g of sodium carbonate in 10 ml of water. 0.036 mmol of triphenylphosphino-3,3',3"-trisulfonate trisodium salt (TPPTS) are subsequently added. The mixture is heated at 80° C. for 18 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated off on a rotary evaporator. The residue is crystallized from 50 ml of n-heptane. Yield: 2.7 g of 4-methyl-2'-cyanobiphenyl.

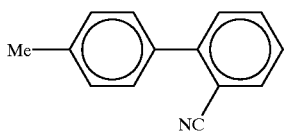

EXAMPLE 3

2-Bromobenzonitrile (3.1 g) and 2.75 g of 4-methylphenyl-boronic acid are dissolved in 20 ml of toluene and 10 ml of ethanol. The solution is admixed with 40.4 mg (1 mol %) of palladium(II) acetate and 4.47 g of sodium carbonate in 10 ml of water. 0.18 mmol of BINAS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated off on a rotary evaporator. The residue is crystallized from 50 ml of n-heptane. Yield: 2.55 g of 4-methyl-2'-cyanobiphenyl.

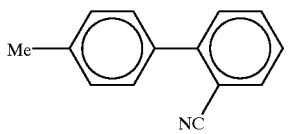

EXAMPLE 4

2-Bromobenzonitrile (3.1 g) and 2.75 g of 4-methylphenyl-boronic acid are dissolved in 20 ml of toluene and 10 ml of ethanol. The solution is admixed with 4 mg (0.1 mol %) of palladium(II) acetate and 4.47 g of sodium carbonate in 10 ml of water. 0.018 mmol of BINAS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated off on a rotary evaporator. The residue is crystallized from 50 ml of n-heptane. Yield: 2.45 g of 4-methyl-2'-cyanobiphenyl.

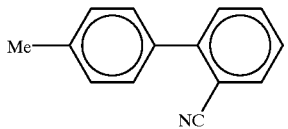

EXAMPLE 5

10.43 g (0.044 mol) of 2,5-dibromopyrimidine, 10 g (0.044 mol) of 4-(phenylmethoxy)benzeneboronic acid, 98.8 mg (0.00044 mol) of palladium(II) acetate, (0.001752 mol) of TPPTS and 9.3 g (0.0876 mol) of sodium carbonate are heated at 80° C. in 100 ml of toluene, 50 ml of ethanol and 30 ml of water for 48 hours. The palladium catalyst is subsequently separated off from the reaction mixture by filtration at 80° C. The lower aqueous phase of the reaction mixture is separated off at 80° C. before the organic phase is freed of the solvents on a rotary evaporator and is dried in a high vacuum. The crude product thus obtained is crystallized from acetonitrile (300 ml), giving 14.5 g (93% yield, based on 2,5-dibromopyrimidine) of 5-bromo-2-[4-(phenylmethoxy)phenyl]-pyrimidine (content according to HPLC: 98%).

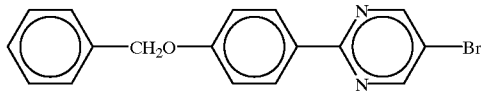

EXAMPLE 6

2-Bromobenzonitrile (3.1 g) and 2.75 g of 4-methylphenyl-boronic acid are dissolved in 20 ml of toluene and 10 ml of ethanol. The solution is admixed with 108.5 mg (1 mol %) of bis(dibenzylideneacetone)palladium (Pd(dba)$_2$) and 4.47 g of sodium carbonate in 10 ml of water. 0.36 mmol of triphenylphosphino-3,3',3"-trisulfonate trisodium salt (TPPTS) is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane. Yield: 2.91 g of 4-methyl-2'-cyanobiphenyl, melting point 49° C.

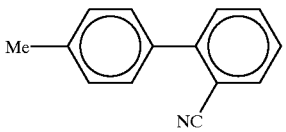

EXAMPLE 7

2-Bromobenzonitrile (3.1 g) and 2.75 g of 4-methylphenyl-boronic acid are dissolved in 20 ml of toluene and 10 ml of ethanol. The solution is admixed with 10.4 mg (0.1 mol %) of Pd(dba)$_2$ and 4.47 g of sodium carbonate in 10 ml of water. 0.036 mmol of triphenylphosphino-3,3',3"-trisulfonate trisodium salt (TPPTS) is subsequently added. The mixture is heated at 80° C. for 18 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane. Yield: 2.69 g of 4-methyl-2'-cyanobiphenyl.

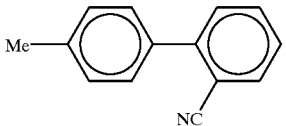

EXAMPLE 8

2-Bromobenzonitrile (3.1 g) and 2.75 g of 4-methylphenyl-boronic acid are dissolved in 20 ml of toluene and 10 ml of ethanol. The solution is admixed with 103.5 mg (0.1 mol %) of Pd(dba)$_2$ and 4.47 g of sodium carbonate in 10 ml of water. 0.18 mmol of BINAS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane. Yield: 2.5 g of 4-methyl-2'-cyanobiphenyl.

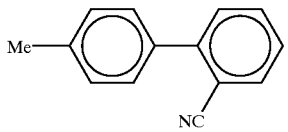

EXAMPLE 9

2-Bromobenzonitrile (3.1 g) and 2.75 g of 4-methylphenyl-boronic acid are dissolved in 20 ml of toluene and 10 ml of ethanol. The solution is admixed with 10.4 mg (0.1 mol %) of Pd(dba)$_2$ and 4.47 g of sodium carbonate in 10 ml of water. 0.018 mmol of BINAS is subsequently added. The mixture is heated at 80° C. for 12 hours. After the reaction is complete, the mixture is cooled to room temperature and the organic phase is separated off. The aqueous phase is extracted three times by shaking with dichloromethane. The combined organic phases are dried over magnesium sulfate and the solvents are subsequently evaporated on a rotary evaporator. The residue is crystallized from 50 ml of n-heptane. Yield: 2.5 g of 4-methyl-2'-cyanobiphenyl.

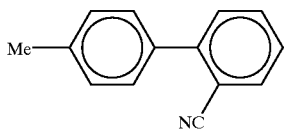

EXAMPLE 10

10.43 g (0.044 mol) of 2,5-dibromopyrimidine, 10 g (0.044 mol) of 4-(phenylmethoxy)benzeneboronic acid, 253 mg (0.00044 mol) of Pd(dba)$_2$, (0.001752 mol) of TPPTS and 9.3 g (0.0876 mol) of sodium carbonate are heated at 80° C. in 100 ml of toluene, 50 ml of ethanol and 30 ml of water for 48 hours. The palladium catalyst is subsequently separated at 80° C. from the reaction mixture by filtration. The lower aqueous phase of the reaction mixture is separated off at 80° C. before the organic phase is freed of the solvents on a rotary evaporator and is dried in a high vacuum. The crude product thus obtained is crystallized from acetonitrile (300 ml), giving 14.7 g (93% yield, based on 2,5-dibromopyrimidine) of 5-bromo-2-[4-(phenylmethoxy)phenyl]pyrimidine (content according to HPLC: 98%).

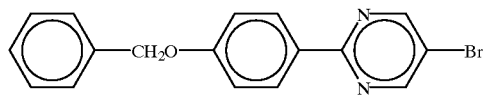

EXAMPLE 11

Using a method similar to Example 10, 27.7 g (100 mmol) of 5-[1,3,2]-dioxaborolane-2-yl-2-octyloxypyridine and 28.9 g (100 mmol) of 5-bromo-2-octyloxypyrimidine, 0.288 g (0.5 mmol) of Pd(dba)$_2$, 2 mmol of TPPTS and 21.2 g (200 mmol) of sodium carbonate give, after chromatography on silica gel, 39.6 g (96%) of product.

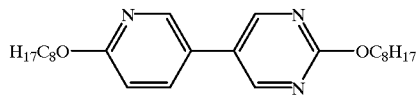

Phase sequence: X 64 S$_C$ 67 S$_A$ 91 I

EXAMPLE 12

Using a method similar to Example 10, 24.3 g (100 mmol) of 2-bromo-5-hexylpyrimidine and 21.9 g (100 mmol) of 4-hexyloxybenzeneboronic acid, 0.288 g (0.5 mmol) of Pd(dba)$_2$, 2 mmol of BINAS and 21.2 g (200 mmol) of sodium carbonate give, after chromatography on silica gel, 32.4 g (95%) of product.

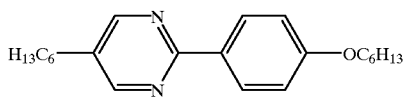

Phase sequence: X$_1$ 15 X$_2$ 32N 61 I

We claim:

1. A process for preparing polycyclic aromatic compounds by cross-coupling aromatic boron compounds with aromatic halogen compounds or perfluoroalkylsulfonates under palladium catalysis in the presence of at least one water-soluble complexing ligand, wherein the reaction medium forms an aqueous and an organic phase and the palladium is added in the form of a palladium compound soluble in the organic phase.

2. The process as claimed in claim 1, wherein a polycyclic aromatic compound of the formula (XII),

$$R^1(-A^1)_k(-M^1)_1-A^2-A^3(-M^2)_m(-A^4)_n-R^2 \quad (XII)$$

where the symbols and indices have the following meanings:
R$^1$ and R$^2$ are each, independently of one another, benzyloxy, H, F, Cl, Br, —NC, —CN, —CF$_3$, —OCF$_3$ or a straight-chain, branched (with or without an asymmetric carbon atom) or cyclic alkyl radical having from 1 to 18 carbon atoms, where one or two nonadjacent —CH$_2$— groups can also be replaced by —O—, —S—, —CO—, —CO—O, —O—CO—, —CO—S, —S—CO—, —O—CO—O—, —CH=CH—, —C≡C—, —SO$_2$—, CON(H,C$_1$–C$_8$-alkyl), cyclopropane-1,2-diyl or —Si(CH$_3$)$_2$— and where one or more hydrogen atoms of the alkyl radical can also be replaced by F, Cl, Br or CN;

A$^1$ and A$^4$ are each, independently of one another, 1,4-phenylene, pyrazine-2,5-diyl, pyridazine-3,6-diyl, pyridine-2,5-diyl, pyrimidine-2,5-diyl, trans-1,4-cyclohexylene, naphthalene-2,6-diyl, where one or more hydrogen atoms can be replaced by identical or different substituents L, where L has one of the meanings given under R$^1$ or is 4,4-dimethylisoxazoline, and where one or two nonadjacent —CH$_2$ groups of the cyclohexylene can be replaced by —O— or —S—, or 1,3,4-thiadiazol-2,5-diyl, 1,3-thiazol-2,4-diyl, 1,3-thiazol-2,5 diyl, thiophene-2,4-diyl, thiophene-2,5-diyl, piperazine-1,4-diyl, piperazine-2,5-diyl, piperidine-1,4-diyl, bicyclo[2.2.2]octane-1,4-diyl, $A^2$ and $A^3$ are each, independently of one another, 1,4-phenylene, pyrazine-2,5-diyl, pyridazine-3,6-diyl, pyridine-2,5-diyl, pyrimidine-2,5-diyl, naphthalene-2,6-diyl, where one or more hydrogen atoms can be replaced by identical or different substituents L, where L has one of the meanings given under $R^1$, is 4,4-dimethylisoxazoline or, in the case of $A^3$, is also —CHO, or 1,3,4-thiadiazol-2,5-diyl, 1,3-thiazol-2,4-diyl, 1,3-thiazol-2,5-diyl, thiophene-2,4-diyl or thiophene-2,5-diyl;

$M^1$ and $M^2$ are each, independently of one another, —O—, —S—, —CO—, —CO—O—, —O—CO—, —CO—S—, —S—CO—, —O—CO—O, —$CH_2$—O, —O$CH_2$—, —$CH_2CH_2$—, —CH=CH—, —C≡C—, —CH(CN)—$CH_2$—, —$CH_2$—CH(CN)—, —CH=N—, —N=CH—, —$CH_2CH_2CH_2$—O—, —O$CH_2CH_2CH_2$—, —$CH_2CH_2CO$—O—, —O—COC$H_2CH_2$—;

k, l, m, n are each, independently of one another, zero or one; is prepared by reacting an aromatic boron compound of the formula (VII), $R^1(-A^1)_k(-M^1)_l-A^2-BQ_1Q_2$  (VII)

where $R^1$, $A^1$, $A^2$, $M^1$, k and l are as defined for formula (XII), $Q,Q_2$ are identical or different and are —OH, $C_1$–$C_4$-alkoxy, $C_1$–$C_4$-alkyl, phenyl, which may be unsubstituted or substituted by $C_1$–$C_4$-alkyl, $C_1$–$C_4$-alkoxy or halogen, or are halogen, or $Q_1$ and $Q_2$ together form a $C_1$–$C_4$-alkylenedioxy group, a methylene group which may be unsubstituted or substituted by one or two $C_1$–$C_4$-alkyl group, an aromatic boron compound of the formulas ($IX^1$)

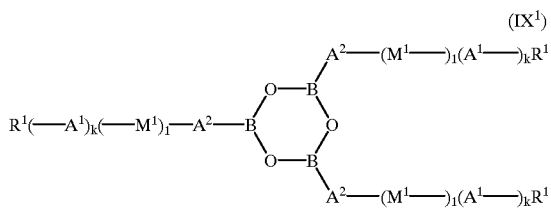

with an aromatic halogen compound or a perfluoroalkylsulfonate of the formula (XI), $X-A^3(-M^2)_m(-A^4)_n-R^2$  (XI)

where $R^2$, $R^3$, $A^3$, $A^4$, $M^2$, m and n are as defined for formula (XII) and X is chlorine, bromine, iodine or $OSO_2$—$C_pF_{2p+1}$, where p has an integral value from 1 to 10.

3. The process as claimed in claim 1, wherein a palladium compound soluble in the organic phase is selected from the group consisting of palladium ketonates, palladium acetylacetonates, (nitrile)-palladium halides, (olefin) palladium halides, palladium halides, allylpalladium halides and palladium biscarboxylates.

4. The process as claimed in claim 3, wherein a palladium compound soluble in the organic phase is selected from the group consisting of bis(benzylideneacetone)palladium(0), bis(benzylideneacetone)palladium(0)-chloroform complex, palladium bisacetylacetonate, palladium dichloride, sodium tetrachloropalladate, dichloro(dimethyl sulfoxide)palladium (II), bis(benzonitrile)palladium dichloride, bis(acetonitrile)palladium dichloride, palladium(II) acetate, palladium(II) propionate, palladium(ll)butanoate and (1c,5c-cyclooctadiene)palladium dichloride.

5. The process as claimed in claim 1, wherein the organic phase comprises one or more water-insoluble solvents selected from the group consisting of hydrocarbons, ethers, higher alcohols which are not completely miscible with water, ketones, amides and nitrites.

6. The process as claimed in claim 1, wherein the aqueous phase of the reaction mixture comprises a water-miscible organic cosolvent selected from the group consisting of nitrites; amides and lower alcohols.

7. The process as claimed in claim 1, wherein at least one compound selected from the group consisting of phosphines, phosphites, phosphinous esters, phosphinous esters, phospholes, bipyridines, phenanthrolines, porphyrins and alizarins is used as a water-soluble complexing ligand.

8. The process as claimed in claim 1, which further comprises at least one base selected from the group consisting of alkali metal and alkaline earth metal hydroxides, alkali metal and alkaline earth metal carbonates, alkali metal hydrogencarbonates, alkali metal and alkaline earth metal acetates, alkali metal and alkaline earth metal alcoholates and primary, secondary and tertiary amines.

9. The process according to claim 2, wherein $Q_1$, $Q_2$ are identical or different and are —OH, $C_1$–$C_4$-alkoxy, $C_1$–$C_4$-alkyl, phenyl, which may be unsubstituted or substituted by $C_1$–$C_4$-alkyl, $C_1$–$C_4$-alkoxy or halogen, or are halogen, or $Q_1$ and $Q_2$ together form a $C_1$–$C_4$-alkylenedioxy group or a methylene group which may be unsubstituted or substituted by one or two $C_1$–$C_4$-alkyl groups.

10. The process according to claim 2 wherein the aromatic boron compound is a compound of the formula ($IX^1$)

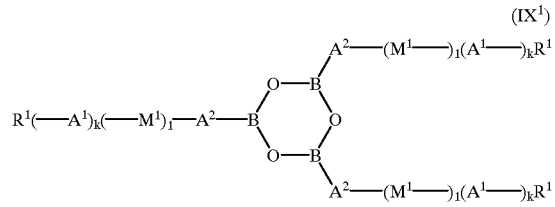

11. In a method for preparing a liquid-crystal mixture, the improvement which comprises using a compound produced in claim 1 as a component in the liquid-crystal mixture or as an intermediate in the synthesis of said component.

12. In a method for preparing an angiotensin II inhibitor, the improvement which comprises using a compound produced in claim 1, as an intermediate.

* * * * *